United States Patent [19]

Glastra

[11] Patent Number: 5,624,450
[45] Date of Patent: Apr. 29, 1997

[54] STENT REMOVAL

[75] Inventor: Hendrik Glastra, Enschede, Netherlands

[73] Assignee: Cordis Corporation, Miami Lakes, Fla.

[21] Appl. No.: 534,639

[22] Filed: Sep. 27, 1995

[30] Foreign Application Priority Data

Sep. 27, 1994 [NL] Netherlands .................... 9401571

[51] Int. Cl.$^6$ .................................................. A61F 11/00
[52] U.S. Cl. ........................ 606/108; 606/192; 606/198
[58] Field of Search ........................... 606/108, 191, 606/192, 194, 198; 623/1, 12; 604/96, 265

[56] References Cited

U.S. PATENT DOCUMENTS

| 4,762,128 | 8/1988 | Rosenbluth . | |
|---|---|---|---|
| 4,893,623 | 1/1990 | Rosenbluth . | |
| 4,990,151 | 2/1991 | Wallsten . | |
| 5,026,377 | 6/1991 | Burton et al. | 606/120 |
| 5,100,429 | 3/1992 | Sinofsky et al. . | |
| 5,197,978 | 3/1993 | Hess | 623/12 |
| 5,199,951 | 4/1993 | Spears | 606/194 |
| 5,312,430 | 5/1994 | Rosenbluth et al. . | |
| 5,411,507 | 5/1995 | Heckele . | |
| 5,474,563 | 12/1995 | Myler et al. | 606/108 |
| 5,534,007 | 7/1996 | St. Bermain et al. | 606/198 |

FOREIGN PATENT DOCUMENTS

| 0274846 | 12/1987 | European Pat. Off. . |
|---|---|---|
| 0575719 | 4/1993 | European Pat. Off. . |

*Primary Examiner*—Sam Rimell
*Assistant Examiner*—Justine Yu
*Attorney, Agent, or Firm*—Lockwood, Alex, Fitzgibbon & Cummings

[57] ABSTRACT

The invention relates to an assembly for the removal of a stent from a body vessel without an operation being necessary to gain access to this stent. This assembly has for this purpose an expandable element, connected to a pulling device, the outer surface of which is covered with an adhesive medium and which, when the element is positioned inside the stent, is expanded and lies with its outer surface against the inner surface of the stent and thereby causes an attachment between this outer surface and the inner surface of the stent. The element with the stent attached to it then can be withdrawn via the body vessel.

19 Claims, 2 Drawing Sheets

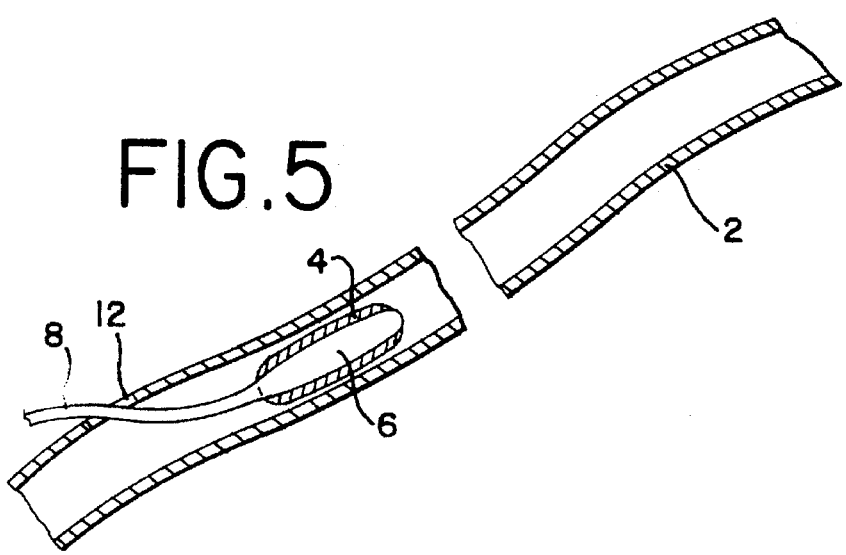
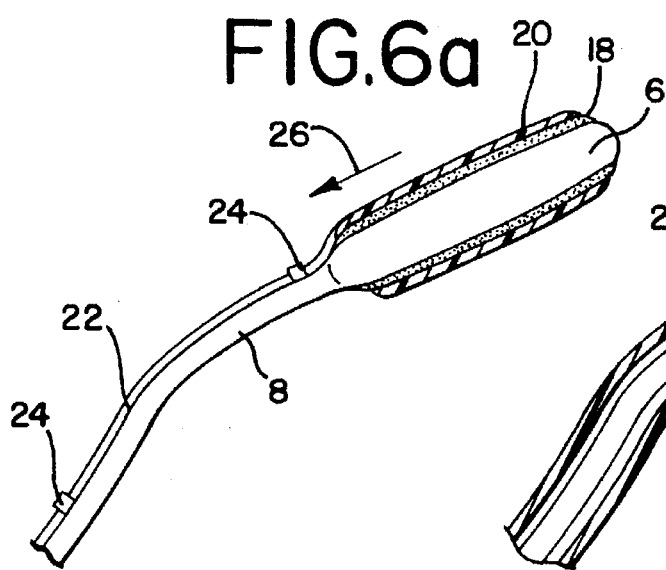
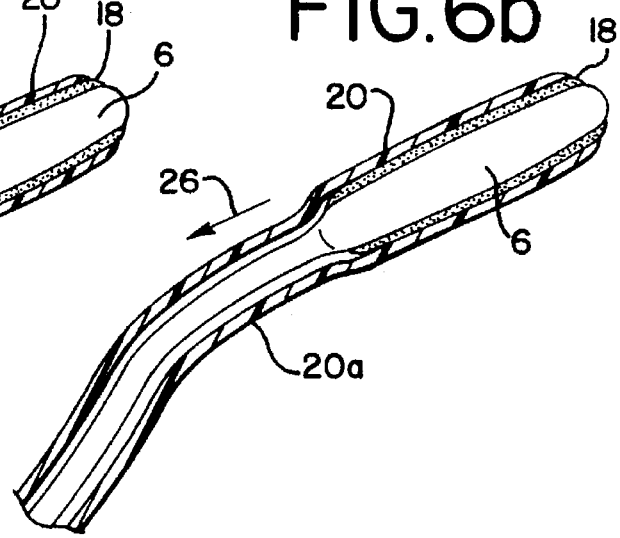
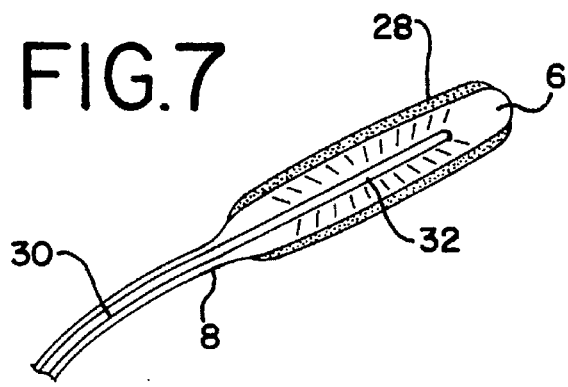

STENT REMOVAL

BACKGROUND AND SUMMARY OF THE INVENTION

The invention relates to an assembly and related method for the removal of a stent from a body vessel.

Methodology of the treatment of vascular afflictions by the introduction of a so-called "stent" into the affected (weakened or locally clogged) body vessel is being developed continuously. A stent is (see for example European patent application 0 452 219) a hollow, often cylindrical, element which is introduced into the body vessel at the desired location by means of a suitable catheter system and supports the wall of the vessel locally.

Afflictions of blood vessels, esophagus, gall ducts and the like can be treated in this manner.

Using the current state of the art, once such a stent expands within the body, it can only be removed by a conventional surgical operation which involves cutting through the patients skin and tissues. This is, of course, especially traumatic and stressful for a patient.

There exists, therefore, a great need for an assembly and method with which it is possible to remove an introduced and deployed stent without requiring operational intervention. The present invention aims to fulfil this need.

In this regard, the invention provides an assembly to achieve the function as described above which is characterized by an expandable element or balloon, connected to a pulling device, the outer surface of which is covered with an adhesive medium and which, when the expandable element or balloon is positioned inside the stent, is expanded and lies with its outer surface against the inner surface of the stent, and brings about an attachment between this outer surface and the inner surface of the stent.

After this attachment has been achieved, the expandable element, with the stent attached to it, can be removed by pulling back the complete unit out of the vessel. It is clear that such an operation is not very stressful for the patient, no more than a normal catheterization procedure.

The expandable element can be hollow and be brought into its expanded state by filling with a medium under pressure. In a suitable embodiment, the expandable element is formed by the balloon of a catheter balloon assembly for percutaneous angioplasty.

The adhesive medium can comprise a pressure-sensitive, or an adhesive which is cured by the action of UV radiation. In this latter case, the assembly will be provided with a radiation guide extending into or close to the balloon. The adhesive medium can also comprise a fast-acting adhesive layer.

The whole expandable element can be protected by or slidably enclosed within a protecting sleeve which is connected to a draw wire guided along the catheter or extending alongside the catheter.

When the expandable element is manipulated into engagement with the stent, a very good attachment will occur between the outer wall of the expandable element and the inner wall of the stent. This has the result that, when the thin expandable element contracts so as to reduce its outer diameter, the stent attached to its outer surface—when the stent is made of compliant material—will likewise contract to a smaller outer diameter and can therefore be more easily removed from the body vessel without requiring fully invasive surgery.

BRIEF DESCRIPTION OF THE DRAWINGS

The invention is explained by way of the accompanying drawings. These relate to an embodiment having a balloon-shaped expandable element. They show schematically and in section:

FIG. 5 illustrates a final phase of extraction of the assembly according to the invention;

FIG. 6a & FIG. 6b further illustrate part of an embodiment of the invention in which use is made of an adhesive layer protected by a sleeve; and FIG. 7 illustrates part of an embodiment of the invention in which use is made of an adhesive which cures by the influence of UV radiation.

DETAILED DESCRIPTION OF THE INVENTION

Figure 1:
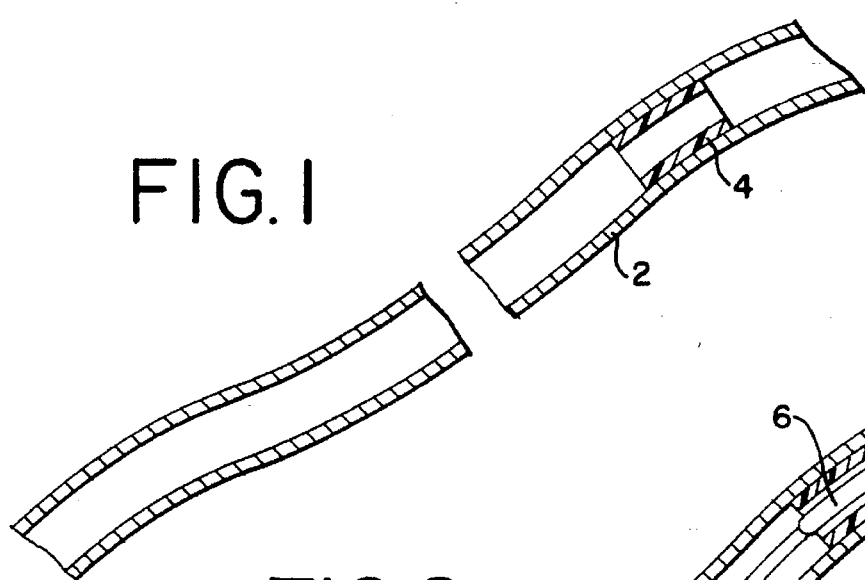
FIG. 1 illustrates a body vessel with a stent introduced into it.

FIG. 1 illustrates a body vessel 2 for example, a vein, esophagus or gall duct having a stent 4 located within it using suitable stent deployment techniques.

Figure 2:
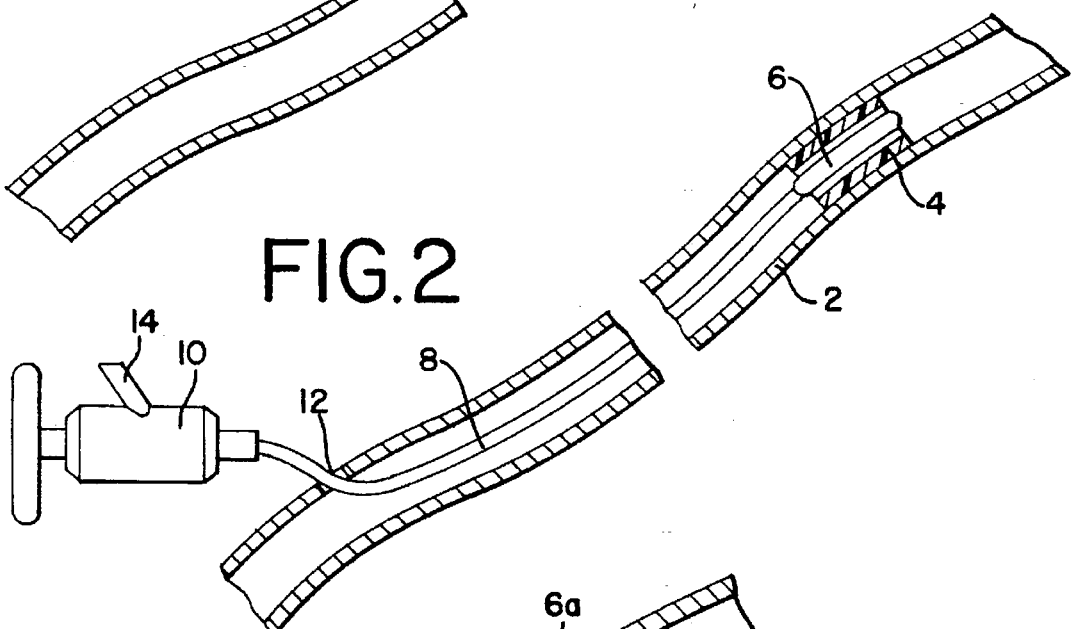
FIG. 2 shows the body vessel within which is positioned the assembly according to the invention, the expandable element of which is positioned at the location of the stent.

For the removal of this stent 4, use is made of an assembly according to the invention in which the expandable element comprises a balloon 6, which is connected to an associated catheter 8 and to a manipulation device 10. (See FIG. 2.) This can be a known and commercially available balloon catheter assembly for percutaneous angioplasty. The balloon 6 is brought to the current location within the body vessel, making use of known methodology. A usual first step in this regard is via an incision 12 in the body vessel 2. Thereafter, a so-called "guide wire" (not shown) is inserted, the catheter 8 with the balloon 6 near its distal end is then slid along this guide wire. The guide wire is then retracted, and the catheter 8 is connected to the manipulation and operating device 10. The latter is provided with a connector 14, shown schematically, for the supply of the expansion fluid under a selected elevated pressure into the balloon 6, which pressure is well in excess of normal atmospheric pressure.

Figure 3:
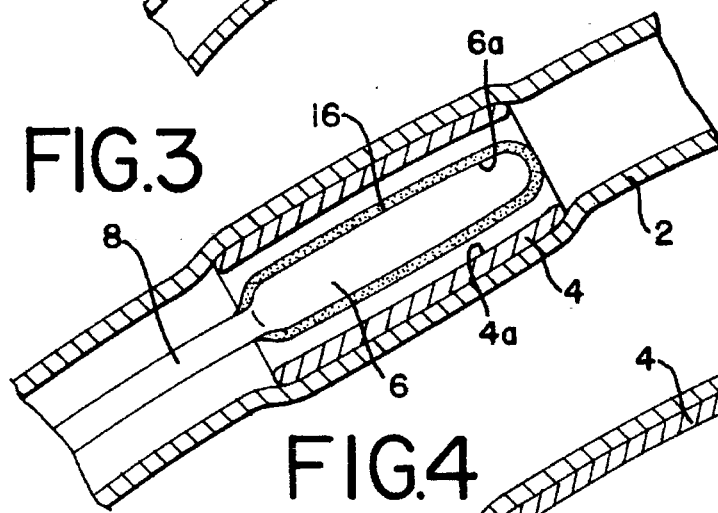
FIG. 3 illustrates on an enlarged scale, the stent with the as yet unexpanded, expandable element positioned inside it.

FIG. 3 shows the body vessel 2 on an enlarged scale, with the stent 4 implanted in it. Also shown is the still folded balloon 6 and the distal part of the catheter 8.

According to the invention, the outer surface of the balloon 6 is covered with an adhesive layer 16, which in this case comprises a pressure-sensitive adhesive, that is an adhesive which, when the outer surface 6a of the balloon 6 is expanded with a selected elevated pressure to be pressed against the inner surface 4a of the stent 4, brings about a very strong bond between these two surfaces 4a, 6a.

Figure 4:
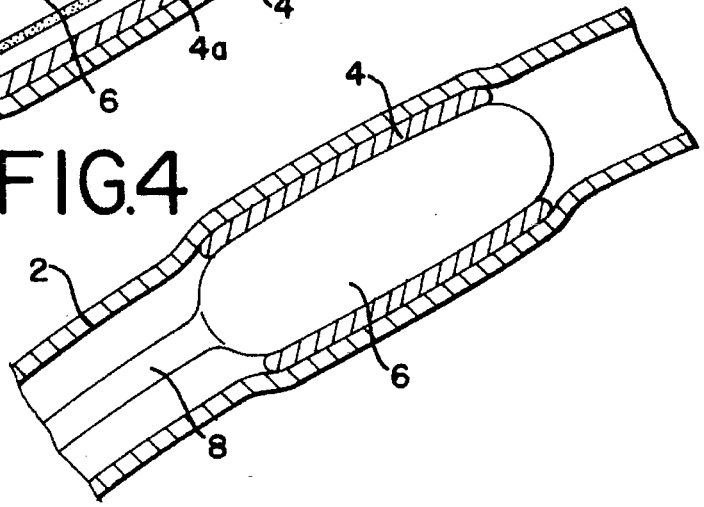
FIG. 4 shows the stent with the expandable element now radially expanded so as to be brought into contact with the stent.

FIG. 4 shows the following situation. By the supply of fluid under pressure into the inside of the balloon 6, the two surfaces 42, 62 are pressed against each other with the desired force, and the adhesive layer 16 provides the attachment between them. The balloon 6 can now, as shown in FIG. 5, by exerting a pulling force on the catheter 8, be pulled back and removed together with the stent 4 via the incision 12.

A very good attachment will thus occur between the outer wall of the balloon and the inner wall of the stent. This has the result that, when the balloon contracts following reduction of the pressure inside of it, the stent attached to the outer surface of the balloon will—when the stent is made of compliant material—likewise reduce to a smaller outer diameter and can therefore be more easily removed.

FIG. 6a illustrates an embodiment of the present invention in which the attachment layer 18 on the outer surface of the balloon 6 is covered with a protecting sleeve 20. This sleeve 20 is connected to a strand, or draw string 22, which is led along the catheter 8, for example by means of suitable guides 24.

After the balloon 6 has been positioned at the correct location, the sleeve 20 is pulled back in the direction of the arrow 26, and the balloon 6 is expanded. Following this, the complete unit is removed in the previously described manner.

The sleeve 20 can also, as shown in FIG. 6b, continue as a part 20a, extending along the full length of the catheter, upon which a pulling force can be exercised in the direction of the arrow 26.

It is also conceivable to use an adhesive which is cured under the influence of UV radiation. FIG. 7 shows a suitable embodiment for this. This comprises a balloon 6, provided with a thin layer 28 of adhesive, which is cured under the influence of UV radiation, on its outer surface. The UV radiation is supplied via a light conducting fiber or cable 30, included inside the catheter 8, of which the proximal end, not shown in the drawing, is irradiated with UV radiation which then emits from the distal end 32 to effect or complete curing and setting of this adhesive.

It is clear that one of skill in the art will be able to select, from the many types of adhesives available, an adhesive or adhesives suited to the embodiments described above, taking into consideration the material and design of the stent to be removed.

I claim:

1. An assembly for the removal of a stent from a body vessel, comprising: a pulling device suitable for slidably moving within the body vessel, an inflatable, expandable element connected to a distal end of said pulling device, the expandable element having an outer surface with an adhesive medium disposed thereon effective to adhere to both said expandable element and the stent when they are being removed from the body vessel, and wherein, when the expandable element is positioned inside the body vessel and within the stent and is then expanded, said outer surface of the expandable element is brought into contact with an inner surface of the stent, thereby effecting an attachment and the adhesion between said outer surface of the expandable element and the inner surface of the stent such that the stent adhered thereto can be removed by pulling on said pulling device.

2. The assembly in accordance with claim 1, wherein said expandable element is hollow and is expandable by filling said expandable element with a medium under pressure.

3. The assembly in accordance with claim 2, wherein said expandable element is a balloon of a catheter balloon assembly for percutaneous angioplasty.

4. The assembly in accordance with claim 1, wherein said adhesive medium is a pressure-sensitive adhesive.

5. The assembly in accordance with claim 1, wherein said adhesive medium is a curable adhesive which is cured under the influence of UV radiation.

6. The assembly in accordance with claim 5, further including a radiation guide extending near said expandable element and into proximity to said curable adhesive.

7. The assembly in accordance with claim 1, wherein said adhesive medium is a fast-acting adhesive.

8. The assembly in accordance with claim 1, further including a protective sleeve placed around said adhesive medium, said protective sleeve extending for substantially the entire length of said pulling device.

9. The assembly in accordance with claim 1, wherein said pulling device includes an elongated catheter and said expandable element includes an inflatable catheter balloon, said protective sleeve extending over said catheter balloon and including means for withdrawing said protective sleeve from its placement around said adhesive medium.

10. A stent removal assembly for insertion into a body vessel and removal of a stent previously implanted into the body vessel, the assembly comprising:

a removal instrument for traversing a length of said body vessel, the removal instrument having a distal end for insertion into said body vessel and a proximal end for manipulating said removal instrument, said removal instrument having a selectively expandable element disposed at said distal end of said removal instrument, the expandable element being selectively expandable from a first insertion dimension wherein said expandable element fits within said body vessel to a second removal dimension wherein said expandable element abuts an interior surface of the stent which is to be removed from the body vessel, said expandable element having an outer surface with an adhesive medium disposed thereon which is brought into contact with the interior surface of the stent implanted in the body vessel when said expandable element is expanded to said second removal dimension, said adhesive medium being effective to adhere to both said expandable element and the stent when they are being removed from the body vessel by withdrawing said removal instrument from the body vessel.

11. The stent removal assembly as defined in claim 10, wherein said removal instrument is a balloon catheter and said expandable element is an expandable balloon.

12. The stent removal assembly as defined in claim 11, wherein said adhesive medium is a radiation-curable adhesive and said catheter includes means disposed within said catheter for conveying radiation to said adhesive medium in order to cure said radiation-curable adhesive in place within said blood vessel.

13. The stent removal assembly as defined in claim 12, wherein said radiation conveying means includes a fiber optic cable and said radiation-curable adhesive is curable upon exposure to UV radiation, said fiber optic cable transmitting UV radiation thereby to said distal end of said removal instrument.

14. The stent removal assembly as defined in claim 11, wherein said assembly includes a protective sleeve overlying said adhesive medium to prevent premature contact between said adhesive medium and said stent, the protective sleeve including a retrieval element extending along said catheter for removing said protective sleeve from said adhesive medium.

15. The stent removal assembly as defined in claim 11, wherein said assembly includes a protective sleeve overlying said adhesive medium, said protective sleeve extending substantially over the length of said catheter.

16. The stent removal assembly as defined in claim 10, wherein said adhesive medium is a pressure-sensitive adhesive.

17. The stent removal assembly as defined in claim 10, wherein said adhesive medium is a fast setting adhesive.

18. A stent removal assembly for insertion into a body vessel and removal of a stent previously implanted into the body vessel, the assembly comprising:

a removal instrument for traversing a length of said body vessel, the removal instrument having a distal end for insertion into said body vessel and a proximal end for manipulating said removal instrument, said removal instrument having a selectively expandable element disposed at said distal end of said removal instrument, the expandable element being selectively expandable from a first insertion dimension wherein said expandable element fits within said body vessel to a second removal dimension wherein said expandable element abuts an interior surface of the stent which is to be removed from the body vessel, said expandable element having an outer surface with an adhesive medium disposed thereon which is brought into contact with the interior surface of the stent implanted in the body vessel when said expandable element is expanded to said second removal dimension, said adhesive medium being effective to adhere to both said expandable element and the stent when they are being removed from the body vessel by withdrawing said removal instrument from the body vessel, said adhesive medium being a radiation-curable adhesive and said expandable element includes means disposed therein for conveying radiation to said adhesive medium in order to cure said radiation-curable adhesive in place within the body vessel.

19. The stent removal assembly as defined in claim 18, wherein said radiation conveying means includes a fiber optic cable and said radiation-curable adhesive is curable upon exposure to UV radiation, said fiber optic cable transmitting UV radiation thereby to said distal end of said removal instrument.

* * * * *

UNITED STATES PATENT AND TRADEMARK OFFICE
CERTIFICATE OF CORRECTION

PATENT NO. : 5,624,450
DATED : April 29, 1997
INVENTOR(S) : Hendrik Glastra

It is certified that error appears in the above-indentified patent and that said Letters Patent is hereby corrected as shown below:

Column 2, line 62: delete "42, 62" and insert --4a, 6a--.

Signed and Sealed this

Seventh Day of October, 1997

Attest:

BRUCE LEHMAN

Attesting Officer

Commissioner of Patents and Trademarks